(12) United States Patent
Dershem et al.

(10) Patent No.: US 8,158,748 B2
(45) Date of Patent: Apr. 17, 2012

(54) HETERO-FUNCTIONAL COMPOUNDS AND METHODS FOR USE THEREOF

(75) Inventors: Stephen M. Dershem, San Diego, CA (US); Farhad G Mizori, San Diego, CA (US)

(73) Assignee: Designer Molecules, Inc., San Diego, CA (US)

(*) Notice: Subject to any disclaimer, the term of this patent is extended or adjusted under 35 U.S.C. 154(b) by 149 days.

(21) Appl. No.: 12/541,147

(22) Filed: Aug. 13, 2009

(65) Prior Publication Data

US 2010/0041845 A1    Feb. 18, 2010

Related U.S. Application Data

(60) Provisional application No. 61/088,608, filed on Aug. 13, 2008.

(51) Int. Cl.
*C08F 16/32* (2006.01)

(52) U.S. Cl. ........ 528/405; 526/280; 526/281; 526/282; 526/283; 526/284; 526/308; 526/309; 526/313; 526/320; 526/327; 526/328; 526/328.5; 526/329.5; 526/330; 526/332; 526/333; 526/334; 560/205; 560/220; 560/221; 560/225; 528/361; 528/403; 528/421

(58) Field of Classification Search .......... 526/280, 526/281, 282, 283, 284, 308, 309, 313, 320, 526/327, 328, 328.5, 329.5, 330, 332, 333, 526/334; 560/205, 220, 221, 225; 528/361, 528/403, 405, 421
See application file for complete search history.

(56) References Cited

U.S. PATENT DOCUMENTS

| | | | |
|---|---|---|---|
| 3,905,820 A | 9/1975 | Frass | |
| 4,395,462 A | 7/1983 | Polmanteer | |
| 4,968,738 A | 11/1990 | Dershem | |
| 5,045,127 A | 9/1991 | Dershem et al. | |
| 5,064,480 A | 11/1991 | Dershem et al. | |
| 5,232,962 A | 8/1993 | Dershem et al. | |
| 5,306,333 A | 4/1994 | Dershem et al. | |
| 5,358,992 A | 10/1994 | Dershem et al. | |
| 5,403,389 A | 4/1995 | Dershem | |
| 5,437,964 A | 8/1995 | Lapin et al. | |
| 5,447,988 A | 9/1995 | Dershem et al. | |
| 5,489,641 A | 2/1996 | Dershem | |
| 5,646,241 A | 7/1997 | Dershem et al. | |
| 5,714,086 A | 2/1998 | Osuna et al. | |
| 5,717,034 A | 2/1998 | Dershem et al. | |
| 5,718,941 A | 2/1998 | Dershem et al. | |
| 5,753,748 A | 5/1998 | Dershem et al. | |
| 5,861,111 A | 1/1999 | Dershem et al. | |
| 5,969,036 A | 10/1999 | Dershem | |
| 5,973,166 A | 10/1999 | Mizori et al. | |
| 6,034,150 A | 3/2000 | Hoyle et al. | |
| 6,034,194 A | 3/2000 | Dershem | |
| 6,034,195 A | 3/2000 | Dershem | |
| 6,048,953 A | 4/2000 | Kawashima et al. | |
| 6,121,358 A | 9/2000 | Dershem et al. | |
| 6,187,886 B1 | 2/2001 | Husson et al. | |
| 6,211,320 B1 | 4/2001 | Dershem et al. | |
| 6,300,456 B1 | 10/2001 | Musa | |
| 6,355,750 B1 | 3/2002 | Herr | |
| 6,369,124 B1 | 4/2002 | Hoyle et al. | |
| 6,423,780 B1 | 7/2002 | Dershem et al. | |
| 6,429,281 B1 | 8/2002 | Dershem et al. | |
| 6,521,731 B2 | 2/2003 | Dershem et al. | |
| 6,620,946 B2 | 9/2003 | Dershem et al. | |
| 6,699,929 B2 | 3/2004 | Musa et al. | |
| 6,743,852 B2 | 6/2004 | Dershem et al. | |
| 6,750,301 B1 | 6/2004 | Bonneau et al. | |
| 6,790,597 B2 | 9/2004 | Dershem | |
| 6,825,245 B2 | 11/2004 | Dershem | |
| 6,831,132 B2 | 12/2004 | Liu et al. | |
| 6,852,814 B2 | 2/2005 | Dershem et al. | |
| 6,855,745 B2 | 2/2005 | Hoyle et al. | |
| 6,908,957 B2 | 6/2005 | Musa et al. | |
| 6,916,856 B2 | 7/2005 | Dershem | |
| 6,946,523 B2 | 9/2005 | Dershem et al. | |
| 6,960,636 B2 | 11/2005 | Dershem et al. | |
| 6,963,001 B2 | 11/2005 | Dershem et al. | |
| 7,102,015 B2 | 9/2006 | Dershem et al. | |
| 7,157,587 B2 | 1/2007 | Mizori et al. | |

(Continued)

FOREIGN PATENT DOCUMENTS

| | | |
|---|---|---|
| EP | 1156034 | 11/2001 |
| EP | 1156036 | 11/2001 |
| EP | 1834969 | 9/2007 |
| JP | 2003002919 | 1/2003 |
| WO | 2004099331 | 11/2004 |
| WO | WO-2005121190 | 12/2005 |

(Continued)

OTHER PUBLICATIONS

Adamson, "Review of CSP and Flip Chip Underfill Processes and When to Use the Right Dispensing Tools for Efficient Manufacturing", *Paper Presented at GlobalTRONICS Technology Conference*,Singapore 2002, 1-6.

Andersson, et al., "Initiator-Free Photopolymerization of an Aliphatic Vinyl Ether-Maleimide Monomer", *J Coatings Tech* 69: 1997, 91-95.

Fouassier, , "Photoinitiation, Photopolymerization, and Photocuring", *Hanser/Gardner* 1995, 276-283.

Kohli, et al., "Co-Polymerization of Maleimides and Vinyl Ethers: A Structural Study", *Macromolecules* 31: 1998, 5681-5689.

*Primary Examiner* — Vasu Jagannathan
*Assistant Examiner* — Richard A Huhn
(74) *Attorney, Agent, or Firm* — The Law Offices of Jane K. Bablinm Professional Corporation; Jane K. Babin

(57) ABSTRACT

The invention provides hetero-functional compound compounds useful in a variety of adhesive applications. More particularly, the invention provides compounds bearing at least one electron rich olefinic bond and at least one electron poor olefinic bond, wherein the two olefinic bonds are separated by a $C_3$ to about $C_{500}$ aliphatic, cycloaliphatic, or aromatic spacer.

7 Claims, No Drawings

U.S. PATENT DOCUMENTS

| | | |
|---|---|---|
| 7,176,044 B2 | 2/2007 | Forray et al. |
| 7,199,249 B2 | 4/2007 | Liu et al. |
| 7,208,566 B2 | 4/2007 | Mizori et al. |
| 7,285,613 B2 | 10/2007 | Dershem et al. |
| 7,309,724 B2 | 12/2007 | Dershem et al. |
| 7,326,754 B2 | 2/2008 | Nikolic et al. |
| 7,517,925 B2 | 4/2009 | Dershem et al. |
| 7,678,879 B2 | 3/2010 | Dershem |
| 2002/0010281 A1 | 1/2002 | Musa et al. |
| 2002/0062923 A1 | 5/2002 | Forray |
| 2002/0099168 A1 | 7/2002 | Dershem et al. |
| 2002/0188137 A1 | 12/2002 | Dershem et al. |
| 2002/0193541 A1 | 12/2002 | Dershem et al. |
| 2002/0198356 A1 | 12/2002 | Dershem et al. |
| 2003/0008992 A1 | 1/2003 | Dershem et al. |
| 2003/0055121 A1 | 3/2003 | Dershem et al. |
| 2003/0060531 A1 | 3/2003 | Dershem et al. |
| 2003/0087999 A1 | 5/2003 | Dershem et al. |
| 2003/0109666 A1 | 6/2003 | Dershem et al. |
| 2003/0125551 A1 | 7/2003 | Dershem et al. |
| 2003/0199638 A1 | 10/2003 | Liu et al. |
| 2003/0199655 A1* | 10/2003 | Yurugi et al. ............ 526/320 |
| 2003/0208016 A1 | 11/2003 | Dershem et al. |
| 2004/0006166 A1 | 1/2004 | Liu et al. |
| 2004/0019224 A1 | 1/2004 | Dershem et al. |
| 2004/0077798 A1 | 4/2004 | Dershem et al. |
| 2004/0082724 A1 | 4/2004 | Dershem et al. |
| 2004/0102566 A1 | 5/2004 | Forray et al. |
| 2004/0123948 A1 | 7/2004 | Dershem et al. |
| 2004/0225026 A1 | 11/2004 | Mizori et al. |
| 2004/0225045 A1 | 11/2004 | Forray |
| 2004/0225059 A1 | 11/2004 | Mizori et al. |
| 2005/0107542 A1 | 5/2005 | Liu et al. |
| 2005/0136620 A1 | 6/2005 | Dershem et al. |
| 2005/0137277 A1 | 6/2005 | Dershem et al. |
| 2005/0137340 A1 | 6/2005 | Nikolic et al. |
| 2005/0267254 A1 | 12/2005 | Mizori et al. |
| 2005/0272888 A1 | 12/2005 | Dershem et al. |
| 2006/0009570 A1 | 1/2006 | Zychowski |
| 2006/0009578 A1 | 1/2006 | Dershem |
| 2006/0030672 A1 | 2/2006 | Nikolic et al. |
| 2006/0063014 A1 | 3/2006 | Forray |
| 2006/0069232 A1 | 3/2006 | Dershem |
| 2006/0089447 A1 | 4/2006 | Robertson et al. |
| 2006/0142517 A1 | 6/2006 | Dershem |
| 2007/0060683 A1 | 3/2007 | Musa et al. |
| 2007/0155869 A1 | 7/2007 | Dershem et al. |
| 2007/0205399 A1 | 9/2007 | Mizori |
| 2007/0299154 A1 | 12/2007 | Dershem et al. |
| 2008/0017308 A1 | 1/2008 | Dershem et al. |
| 2008/0075961 A1 | 3/2008 | Mizori |
| 2008/0075963 A1 | 3/2008 | Dershem |
| 2008/0075965 A1 | 3/2008 | Dershem |
| 2008/0103240 A1 | 5/2008 | Dershem |
| 2008/0142158 A1 | 6/2008 | Dershem |
| 2008/0146738 A1 | 6/2008 | Dershem |
| 2008/0160315 A1 | 7/2008 | Forray et al. |
| 2008/0191173 A1 | 8/2008 | Dershem et al. |
| 2008/0210375 A1 | 9/2008 | Dershem et al. |
| 2008/0251935 A1 | 10/2008 | Dersham |
| 2008/0257493 A1 | 10/2008 | Dershem |
| 2008/0262191 A1 | 10/2008 | Mizori |
| 2009/0061244 A1 | 3/2009 | Dershem |
| 2009/0215940 A1 | 8/2009 | Dershem |
| 2009/0288768 A1 | 11/2009 | Dershem |
| 2010/0041803 A1 | 2/2010 | Dershem |
| 2010/0041823 A1 | 2/2010 | Dershem |
| 2010/0041832 A1 | 2/2010 | Dershem |
| 2010/0056671 A1 | 3/2010 | Dershem |
| 2010/0063184 A1 | 3/2010 | Dershem |

FOREIGN PATENT DOCUMENTS

| | | |
|---|---|---|
| WO | WO-2007100329 | 9/2007 |
| WO | WO-2008077141 | 6/2008 |
| WO | WO-2008124797 | 10/2008 |
| WO | WO-2008130894 | 10/2008 |
| WO | WO-2010019832 | 2/2010 |

HETERO-FUNCTIONAL COMPOUNDS AND METHODS FOR USE THEREOF

RELATED APPLICATIONS

This application claims the benefit of priority under 35 USC §119 of U.S. Provisional Application Ser. No. 61/088,608 filed Aug. 13, 2008, the entire disclosure of which is incorporated herein by reference.

FIELD OF THE INVENTION

The present invention relates to field of thermosetting compositions, particularly adhesives and coatings, and methods of preparation and uses therefor. In particular, the present invention relates to hetero-functional monomers containing one or more electron rich carbon-carbon double bond and one or more electron poor double bond.

BACKGROUND OF THE INVENTION

As the electronics industry advances, and production of light weight components increases, the development of new materials gives producers increased options for further improving the performance and ease of manufacture of such components. Adhesive compositions are used for a variety of purposes in the fabrication and assembly of semiconductor packages and microelectronic devices. The more prominent uses include bonding of electronic elements such as integrated circuit (IC) chips to lead frames or other substrates, and bonding IC chips to other IC chips. Adhesives useful for electronic packaging applications typically exhibit properties such as good mechanical strength, curing properties that do not affect the component or the carrier, and rheological properties compatible with application to microelectronic and semiconductor components. Other applications within microelectronic assembly include encapsulants, glob tops, UV lid seal applications and the like.

The demand for smaller and more powerful electronic components presents certain challenges to the microelectronic packaging industry. One way to include more semiconductor die in a component without increasing circuit board area is to arrange the die in a stacked configuration. Indeed, "stacked die" packages conserve "circuit board real estate" without sacrificing power or performance of the electronic component. In addition, the die used in stacked die applications are becoming ever thinner, requiring new adhesive solutions in order to preserve the integrity of these very thin die.

Moreover, other configurations of computer chips on circuit board such as those that require direct attachment to a substrate or board (e.g. "Flip Chips"), required similar properties to achieve higher speed and chip density on circuit boards. Yet with high density and direct contact between circuit boards and chips, there is concern about the thermomechanical expansion mismatch between the chip and the substrate or board, as well as concern that moisture can cause problems with tiny solder joints.

Thus, the microelectronics industry continues to require new adhesives that are able to meet its varying demands. Accordingly, there is a need for the development of materials to address the requirements of this rapidly evolving industry.

SUMMARY OF THE INVENTION

The present invention provides hetero-functional monomers useful in a variety of applications. Specifically, the invention provides compounds that include at least one first moiety comprising an unsubstituted or a substituted group having an electron rich olefinic bond, where a substituent in the substituted group is an acyclic group; at least one second moiety comprising an electron poor olefinic bond; and a linking moiety bridging the first moiety to the second moiety, the linking moiety comprising a $C_3$ to about $C_{500}$ aliphatic, cycloaliphatic, or aromatic group, with the further proviso that when the second moiety is a maleimide group, the linking moiety is free of carbonyl groups.

For example, the first moiety can be derived from a vinyl ethers or and allyl ether. The second moiety can, for example, be derived from a maleate, a fumarate, a maleimide, an acrylate, or a methacrylate.

In certain embodiments, the linking moiety is selected from a $C_4$ to about $C_{500}$ aliphatic, cycloaliphatic, and aromatic group. In other embodiments, the linking moiety is a $C_6$ to about $C_{500}$ aliphatic, cycloaliphatic, or aromatic group. In yet further embodiments, the linking moiety is a $C_8$ to about $C_{500}$ aliphatic, cycloaliphatic, or aromatic group. The linking moiety can also be a $C_{12}$ to about $C_{500}$ aliphatic, cycloaliphatic, or aromatic group.

In one embodiment, a compound according to the invention has a structure represented by formula I:

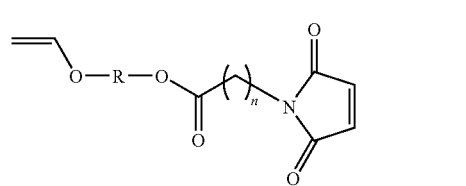

Where R is an alkylene moiety, and n is the integer having the value between 6 and 11. In some aspects of the invention n is at least 8 or at least 10.

Exemplary compounds according to the invention are also provided herein.

Also provided are compositions that include an invention compound. Such compositions may also include at least one curing initiator, co-monomer, co-curing compound, coupling agent, or filler. Co-monomer and co-curing compounds suitable for the compositions of the invention include epoxies, acrylates, methacrylates, maleimides, citraconimides, itaconimides, vinyl ethers, vinyl esters, styrenic compounds, itaconates, fumarates, maleates, allyl functional compounds, oxetanes, benzoxazines, and oxazolines.

The compositions of the invention can be adhesive composition or other types of formulations, such as coatings. Both cured and uncured adhesive compositions are encompassed by the invention. Certain adhesive compositions of the invention are suitable for use in die-attach application.

In yet another aspect of the invention, compositions are provided that include polymers of a plurality of compounds described herein above, where the plurality of compounds are polymerized through the at least one electron rich olefinic bond; and retain pendant moieties containing the at least one electron poor olefinic bond.

DETAILED DESCRIPTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art, such as those set forth in "IUPAC Compendium of Chemical Terminology: IUPAC Recommendations (The Gold Book)" (McNaught ed.; International Union of Pure and Applied Chemistry, $2^{nd}$ Ed., 1997) and "Compendium of Polymer Terminology and Nomenclature: IUPAC Recommendations 2008" (Jones et al., eds; International Union of Pure and Applied Chemistry, 2009). Standard chemical symbols are used interchangeably with the full names represented by such symbols. Thus, for example, the terms "hydrogen" and "H" are understood to have identical meaning. Standard techniques may be used for chemical syntheses, chemical analyses, and formulation.

DEFINITIONS

"About" as used herein means that a number referred to as "about" comprises the recited number plus or minus 1-10% of that recited number. For example, "about" 100 degrees can mean 95-105 degrees or as few as 99-101 degrees depending on the situation. Whenever it appears herein, a numerical range such as "1 to 20" refers to each integer in the given range; e.g., "1 to 20 carbon atoms" means that an alkyl group can contain only 1 carbon atom, 2 carbon atoms, 3 carbon atoms, etc., up to and including 20 carbon atoms (although the term "alkyl" also includes instances where no numerical range of carbon atoms is designated).

"Adhesive" or "adhesive compound" as used herein, refers to any substance that can adhere or bond two items together. Implicit in the definition of an "adhesive composition" or "adhesive formulation" is the fact that the composition or formulation is a combination or mixture of more than one species, component or compound, which can include adhesive monomers, oligomers, and/or polymers along with other materials, whereas an "adhesive compound" refers to a single species, such as an adhesive polymer or oligomer.

More specifically, adhesive composition refers to un-cured mixtures in which the individual components in the mixture retain the chemical and physical characteristics of the original individual components of which the mixture is made. Adhesive compositions are typically malleable and may be liquids, paste, gel or another form that can be applied to an item so that it can be bonded to another item.

"Cured adhesive," "cured adhesive composition" or "cured adhesive compound" refers to adhesives components and mixtures obtained from reactive curable original compound(s) or mixture(s) thereof which have undergone a chemical and/or physical changes such that the original compound(s) or mixture(s) is(are) transformed into a solid, substantially non-flowing material. A typical curing process may involve crosslinking.

"Curable" means that an original compound(s) or composition material(s) can be transformed into a solid, substantially non-flowing material by means of chemical reaction, crosslinking, radiation crosslinking, or the like. Thus, adhesive compositions of the invention are curable, but unless otherwise specified, the original compound(s) or composition material(s) is(are) not cured.

"Thermoplastic," as used herein, refers to the ability of a compound, composition or other material (e.g. a plastic) to dissolve in a suitable solvent or to melt to a liquid when heated and freeze to a solid, often brittle and glassy, state when cooled sufficiently.

"Thermoset," as used herein, refers to the ability of a compound, composition or other material to irreversibly "cure" resulting in a single tridimensional network that has greater strength and less solubility compared to the non-cured product. Thermoset materials are typically polymers that may be cured, for example, through heat (e.g. above 200° Celsius), via a chemical reaction (e.g. epoxy ring opening, free radical polymerization, etc.), or through irradiation (e.g. visible light, U.V., or X-ray irradiation).

Thermoset materials, such as thermoset polymers or resins, are typically liquid or malleable forms prior to curing, and therefore may be molded or shaped into their final form, and/or used as adhesives. Curing transforms the thermoset resin into a rigid infusible and insoluble solid or rubber by a cross-linking process. Thus, energy and/or catalysts are typically added that cause the molecular chains to react at chemically active sites (unsaturated or epoxy sites, for example), linking the polymer chains into a rigid, 3-D structure. The cross-linking process forms molecules with a higher molecular weight and resultant higher melting point. During the reaction, when the molecular weight of the polymer has increased to a point such that the melting point is higher than the surrounding ambient temperature, the polymer becomes a solid material.

"Cross-linking," as used herein, refers to the attachment of two or more oligomer or longer polymer chains by bridges of an element, a molecular group, a compound, or another oligomer or polymer. Crosslinking may take place upon heating; some crosslinking processes may also occur at room temperature or a lower temperature. As cross-linking density is increased, the properties of a material can be changed from thermoplastic to thermosetting.

As used herein, "B-stageable" refers to the properties of an adhesive having a first solid phase followed by a tacky rubbery stage at elevated temperature, followed by yet another solid phase at an even higher temperature. The transition from the tacky rubbery stage to the second solid phase is thermosetting. However, prior to thermosetting, the material behaves similarly to a thermoplastic material. Thus, such adhesives allows for low lamination temperatures while providing high thermal stability.

A "die" or "semiconductor die" as used herein, refers to a small block of semiconducting material, on which a functional circuit is fabricated.

A "flip-chip" semiconductor device is one in which a semiconductor die is directly mounted to a wiring substrate, such as a ceramic or an organic printed circuit board. Conductive terminals on the semiconductor die, usually in the form of solder bumps, are directly physically and electrically connected to the wiring pattern on the substrate without use of wire bonds, tape-automated bonding (TAB), or the like. Because the conductive solder bumps making connections to the substrate are on the active surface of the die or chip, the die is mounted in a face-down manner, thus the name "flip-chip."

"Underfill," "underfill composition" and "underfill material" are used interchangeably to refer to a material, typically polymeric compositions, used to fill gaps between a semiconductor component, such as a semiconductor die, and a substrate. "Underfilling" refers to the process of applying an underfill composition to a semiconductor component-substrate interface, thereby filling the gaps between the component and the substrate.

The term "monomer" refers to a molecule that can undergo polymerization or copolymerization thereby contributing constitutional units to the essential structure of a macromolecule (a polymer).

"Polymer" and "polymer compound" are used interchangeably herein, to refer generally to the combined the products of a single chemical polymerization reaction. Polymers are produced by combining monomer subunits into a covalently bonded chain. Polymers that contain only a single type of monomer are known as "homopolymers," while polymers containing a mixture of monomers are known as "copolymers."

The term "copolymers" is inclusive of products that are obtained by copolymerization of two monomer species, those obtained from three monomers species (terpolymers), those obtained from four monomers species (quaterpolymers), etc. It is well known in the art that copolymers synthesized by chemical methods include, but are not limited to, molecules with the following types of monomer arrangements:

- alternating copolymers, which contain regularly alternating monomer residues;
- periodic copolymers, which have monomer residue types arranged in a repeating sequence;
- random copolymers, which have a random sequence of monomer residue types;
- statistical copolymers, which have monomer residues arranged according to a known statistical rule; and
- block copolymers, which have two or more homopolymer subunits linked by covalent bonds. The blocks of homopolymer within block copolymers, for example, can be of any length and can be blocks of uniform or variable length. Block copolymers with two or three distinct blocks are called diblock copolymers and tri-block copolymers, respectively.

The skilled artisan will appreciate that a single copolymer molecule may have different regions along its length that can be characterized as an alternating, periodic, random, etc. A copolymer product of a chemical polymerization reaction may contain individual polymeric fragments that each differ in the arrangement of monomer units. The skilled artisan will further be knowledgeable in methods for synthesizing each of these types of copolymers, and for varying reaction conditions to favor one type over another.

Furthermore, the length of a polymer chain according to the present invention, will typically vary over a range or average size produced by a particular reaction. The skilled artisan will be aware, for example, of methods for controlling the average length of a polymer chain produced in a given reaction and also of methods for size-selecting polymers after they have been synthesized.

Unless a more restrictive term is used, polymer is intended to encompass homopolymers, and copolymers having any arrangement of monomer subunits as well as copolymers containing individual molecules having more than one arrangement. With respect to length, unless otherwise indicated, any length limitations recited for the polymers described herein are to be considered averages of the lengths of the individual molecules in polymer.

As used herein, "oligomer" or "oligomeric" refers to a polymer having a finite and moderate number of repeating monomers structural units. Oligomers of the invention typically have 2 to about 100 repeating monomer units; frequently 2 to about 30 repeating monomer units; and often 2 to about 10 repeating monomer units; and usually have a molecular weight up to about 3,000.

The skilled artisan will appreciate that oligomers and polymers may, depending on the availability of polymerizable groups or side chains, subsequently be incorporated as monomers in further polymerization or crosslinking reactions.

As used herein, "aliphatic" refers to any alkyl, alkenyl, cycloalkyl, or cycloalkenyl moiety.

"Aromatic hydrocarbon" or "aromatic" as used herein, refers to compounds having one or more benzene rings.

"Alkane," as used herein, refers to saturated straight-chain, branched or cyclic hydrocarbons having only single bonds. Alkanes have general formula $C_nH_{2n+2}$.

"Cycloalkane," refers to an alkane having one or more rings in its structure.

As used herein, "alkyl" refers to straight or branched chain hydrocarbyl groups having from 1 up to about 500 carbon atoms. The terms "alkyl" and "substituted alkyl" include, respectively, substituted and unsubstituted $C_1$-$C_{500}$ straight chain saturated aliphatic hydrocarbon groups, substituted and unsubstituted $C_2$-$C_{200}$ straight chain unsaturated aliphatic hydrocarbon groups, substituted and unsubstituted $C_4$-$C_{100}$ branched saturated aliphatic hydrocarbon groups, substituted and unsubstituted $C_1$-$C_{500}$ branched unsaturated aliphatic hydrocarbon groups.

For example, the definition of "alkyl" includes but is not limited to: methyl (Me), ethyl (Et), propyl (Pr), butyl (Bu), pentyl, hexyl, heptyl, octyl, nonyl, decyl, undecyl, ethenyl, propenyl, butenyl, penentyl, hexenyl, heptenyl, octenyl, nonenyl, decenyl, undecenyl, isopropyl (i-Pr), isobutyl (i-Bu), tert-butyl (t-Bu), sec-butyl (s-Bu), isopentyl, neopentyl, cyclopropyl, cyclobutyl, cyclopentyl, cyclohexyl, cycloheptyl, cyclooctyl, cyclopentenyl, cyclohexenyl, cycloheptenyl, cyclooctenyl, methylcyclopropyl, ethylcyclohexenyl, butenylcyclopentyl, adamantyl, norbornyl and the like.

"Substituted alkyl" refers to alkyl moieties bearing substituents that include but are not limited to alkyl, alkenyl, alkynyl, hydroxy, oxo, alkoxy, mercapto, cycloalkyl, substituted cycloalkyl, heterocyclic, substituted heterocyclic, aryl, substituted aryl (e.g., aryl$C_{1-10}$alkyl or aryl$C_{1-10}$alkyloxy), heteroaryl, substituted heteroaryl (e.g., heteroaryl$C_{1-10}$ alkyl), aryloxy, substituted aryloxy, halogen, haloalkyl (e.g., trihalomethyl), cyano, nitro, nitrone, amino, amido, carbamoyl, =O, =CH—, —C(O)H, —C(O)O—, —C(O)—, —S—, —S(O)$_2$—, —OC(O)—O—, —NR—C(O)—, —NR—C(O)—NR—, —OC(O)—NR—, where R is H or lower alkyl, acyl, oxyacyl, carboxyl, carbamate, sulfonyl, sulfonamide, sulfuryl, $C_{1-10}$alkylthio, aryl$C_{1-10}$alkylthio, $C_{1-10}$alkylamino, aryl$C_{1-10}$alkylamino, N-aryl-N—$C_{1-10}$ alkylamino, $C_{1-10}$alkyl carbonyl, aryl$C_{1-10}$alkylcarbonyl, $C_{1-10}$alkylcarboxy, aryl$C_{1-10}$alkylcarboxy, $C_{1-10}$alkyl carbonylamino, aryl$C_{1-10}$alkylcarbonylamino, tetrahydrofuryl, morpholinyl, piperazinyl, and hydroxypyronyl.

As used herein, "cycloalkyl" refers to cyclic ring-containing groups containing in the range of about 3 up to about 20 carbon atoms, typically 3 to about 15 carbon atoms. In certain embodiments, cycloalkyl groups have in the range of about 4 up to about 12 carbon atoms, and in yet further embodiments, cycloalkyl groups have in the range of about 5 up to about 8 carbon atoms. and "substituted cycloalkyl" refers to cycloalkyl groups further bearing one or more substituents as set forth below.

As used herein, the term "aryl" represents an unsubstituted, mono-, di- or trisubstituted monocyclic, polycyclic, biaryl aromatic groups covalently attached at any ring position capable of forming a stable covalent bond, certain preferred points of attachment being apparent to those skilled in the art (e.g., 3-phenyl, 4-naphtyl and the like). The aryl substituents are independently selected from the group consisting of halo, —OH, —SH, —CN, —NO$_2$, trihalomethyl, hydroxypyronyl, $C_{1-10}$alkyl, aryl$C_{1-10}$alkyl, $C_{1-10}$alkyloxy$C_{1-10}$alkyl, aryl $C_{1-10}$alkyloxy$C_{1-10}$alkyl, $C_{1-10}$alkylthio$C_{1-10}$alkyl, aryl$C_{1-10}$alkylthio$C_{1-10}$alkyl, $C_{1-10}$alkylamino$C_{1-10}$alkyl, aryl$C_{1-10}$alkylamino$C_{1-10}$alkyl, N-aryl-N—$C_{1-10}$alkylamino$C_{1-10}$alkyl, $C_{1-10}$alkylcarbonyl$C_{1-10}$alkyl, aryl $C_{1-10}$alkylcarbonyl $C_{1-10}$alkylcarboxy$C_{1-10}$alkyl, aryl$C_{1-10}$alkylcarboxy$C_{1-10}$alkyl, $C_{1-10}$alkylcarbonylamino$C_{1-10}$alkyl, and aryl$C_{1-10}$alkylcarbonylamino$C_{1-10}$alkyl.

Some specific examples of moieties encompassed by the definition of "aryl" include but are not limited to phenyl, biphenyl, naphthyl, dihydronaphthyl, tetrahydronaphthyl, indenyl, indanyl, azulenyl, anthryl, phenanthryl, fluorenyl, pyrenyl and the like. "Substituted aryl" refers to aryl groups further bearing one or more substituents as set forth below.

As used herein, "arylene" refers to a divalent aryl moiety. "Substituted arylene" refers to arylene moieties bearing one or more substituents as set forth above.

As used herein, "alkylaryl" refers to alkyl-substituted aryl groups and "substituted alkylaryl" refers to alkylaryl groups further bearing one or more substituents as set forth below.

As used herein, "arylalkyl" refers to aryl-substituted alkyl groups and "substituted arylalkyl" refers to arylalkyl groups further bearing one or more substituents as set forth below. Some examples of included but are not limited to (4-hydroxyphenyl)ethyl, or (2-aminonaphthyl)hexenyl.

As used herein, "arylalkenyl" refers to aryl-substituted alkenyl groups and "substituted arylalkenyl" refers to arylalkenyl groups further bearing one or more substituents as set forth below.

As used herein, "arylalkynyl" refers to aryl-substituted alkynyl groups and "substituted arylalkynyl" refers to arylalkynyl groups further bearing one or more substituents as set forth below.

As used herein, "aroyl" refers to aryl-carbonyl species such as benzoyl and "substituted aroyl" refers to aroyl groups further bearing one or more substituents as set forth below.

As used herein, "hetero" refers to groups or moieties containing one or more heteroatoms such as N, O, Si and S. Thus, for example "heterocyclic" refers to cyclic (i.e., ring-containing) groups having e.g. N, O, Si or S as part of the ring structure, and having in the range of 3 up to 14 carbon atoms. "Heteroaryl" and "heteroalkyl" moieties are aryl and alkyl groups, respectively, containing e.g. N, O, Si or S as part of their structure. The terms "heteroaryl", "heterocycle" or "heterocyclic" refer to a monovalent unsaturated group having a single ring or multiple condensed rings, from 1 to 8 carbon atoms and from 1 to 4 hetero atoms selected from nitrogen, sulfur or oxygen within the ring.

The definition of heteroaryl includes but is not limited to thienyl, benzothienyl, isobenzothienyl, 2,3-dihydrobenzothienyl, furyl, pyranyl, benzofuranyl, isobenzofuranyl, 2,3-dihydrobenzofuranyl, pyrrolyl, pyrrolyl-2,5-dione, 3-pyrrolinyl, indolyl, isoindolyl, 3H-indolyl, indolinyl, indolizinyl, indazolyl, phthalimidyl (or isoindoly-1,3-dione), imidazolyl. 2H-imidazolinyl, benzimidazolyl, pyridyl, pyrazinyl, pyradazinyl, pyrimidinyl, triazinyl, quinolyl, isoquinolyl, 4H-quinolizinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, chromanyl, benzodioxolyl, piperonyl, purinyl, pyrazolyl, triazolyl, tetrazolyl, thiazolyl, isothiazolyl, benzthiazolyl, oxazolyl, isoxazolyl, benzoxazolyl, oxadiazolyl, thiadiazolyl, pyrrolidinyl-2,5-dione, imidazolidinyl-2,4-dione, 2-thioxo-imidazolidinyl-4-one, imidazolidinyl-2,4-dithione, thiazolidinyl-2,4-dione, 4-thioxo-thiazolidinyl-2-one, piperazinyl-2,5-dione, tetrahydro-pyridazinyl-3,6-dione, 1,2-dihydro-[1,2,4]tetrazinyl-3,6-dione, [1,2,4,5] tetrazinyl-3,6-dione, dihydro-pyrimidinyl-2,4-dione, pyrimidinyl-2,4,6-trione, 1H-pyrimidinyl-2,4-dione, 5-iodo-1H-pyrimidinyl-2,4-dione, 5-chloro-1H-pyrimidinyl-2,4-dione, 5-methyl-1H-pyrimidinyl-2,4-dione, 5-isopropyl-1H-pyrimidinyl-2,4-dione, 5-propynyl-1H-pyrimidinyl-2,4-dione, 5-trifluoromethyl-1H-pyrimidinyl-2,4-dione, 6-amino-9H-purinyl, 2-amino-9H-purinyl, 4-amino-1H-pyrimidinyl-2-one, 4-amino-5-fluoro-1H-pyrimidinyl-2-one, 4-amino-5-methyl-1H-pyrimidinyl-2-one, 2-amino-1,9-dihydro-purinyl-6-one, 1,9-dihydro-purinyl-6-one, 1H-[1,2,4] triazolyl-3-carboxylic acid amide, 2,6-diamino-N.sub.6-cyclopropyl-9H-purinyl, 2-amino-6-(4-methoxyphenylsulfanyl)-9H-purinyl, 5,6-dichloro-1H-benzoimidazolyl, 2-isopropylamino-5,6-dichloro-1H-benzoimidazolyl, 2-bromo-5,6-dichloro-1H-benzoimidazolyl, and the like. Furthermore, the term "saturated heterocyclic" represents an unsubstituted, mono-, di- or trisubstituted monocyclic, polycyclic saturated heterocyclic group covalently attached at any ring position capable of forming a stable covalent bond, certain preferred points of attachment being apparent to those skilled in the art (e.g., 1-piperidinyl, 4-piperazinyl and the like).

Hetero-containing groups may also be substituted. For example, "substituted heterocyclic" refers to a ring-containing group having in the range of 3 up to 14 carbon atoms that contains one or more heteroatoms and also bears one or more substituents, as set forth above. Examples of substituents include, but are not limited to halo, —OH, —SH, —CN, —NO$_2$, trihalomethyl, hydroxypyronyl, $C_{1-10}$alkyl, aryl$C_{1-10}$alkyl, $C_{1-10}$alkyloxy$C_{1-10}$alkyl, aryl$C_{1-10}$alkyloxy $C_{1-10}$alkyl, $C_{1-10}$alkylthio$C_{1-10}$alkyl, aryl$C_{1-10}$alkylthio$C_{1-10}$alkyl, $C_{1-10}$alkylamino$C_{1-10}$alkyl, aryl$C_{1-10}$alkylamino $C_{1-10}$alkyl, N-aryl-N—$C_{1-10}$alkylamino$C_{1-10}$alkyl, $C_{1-10}$alkylcarbonyl$C_{1-10}$alkyl, aryl$C_{1-10}$alkylcarbonyl $C_{1-10}$alkyl, $C_{1-10}$alkylcarboxy$C_{1-10}$alkyl, aryl$C_{1-10}$alkylcarboxy$C_{1-10}$alkyl $C_{1-10}$alkylcarbonylamino$C_{1-10}$alkyl, and aryl$C_{1-10}$alkylcarbonylamino$C_{1-10}$alkyl.

As used herein, the term "phenol" includes compounds having one or more phenolic functions per molecule. The terms aliphatic, cycloaliphatic and aromatic, when used to describe phenols, refers to phenols to which aliphatic, cycloaliphatic and aromatic residues or combinations of these backbones are attached by direct bonding or ring fusion.

As used herein, "alkenyl," "alkene" or "olefin" refers to straight or branched chain unsaturated hydrocarbyl groups having at least one carbon-carbon double bond, and having in the range of about 2 up to 500 carbon atoms. In certain embodiments, alkenyl groups have in the range of about 5 up to about 250 carbon atoms, 5 up to about 100 carbon atoms, 5 up to about 50 carbon atoms or 5 up to about 25 carbon atoms. In other embodiments, alkenyl groups have in the range of about 6 up to about 500 carbon atoms, 8 up to about 500 carbon atoms, 10 up to about 500 carbon atoms or 20 up to about 500 carbon atoms or 50 up to about 500 carbon atoms. In yet further embodiments, alkenyl groups have in the range of about 6 up to about 100 carbon atoms, 10 up to about 100 carbon atoms, 20 up to about 100 carbon atoms or 50 up to about 100 carbon atoms, while in other embodiments, alkenyl groups have in the range of about 6 up to about 50 carbon atoms, 6 up to about 25 carbon atoms, 10 up to about 50 carbon atoms, or 10 up to about 25 carbon atoms. "Substituted alkenyl" refers to alkenyl groups further bearing one or more substituents as set forth above.

As used herein, "alkylene" refers to a divalent alkyl moiety, and "oxyalkylene" refers to an alkylene moiety containing at least one oxygen atom instead of a methylene (CH$_2$) unit. "Substituted alkylene" and "substituted oxyalkylene" refer to alkylene and oxyalkylene groups further bearing one or more substituents as set forth above.

As used herein, "alkynyl" refers to straight or branched chain hydrocarbyl groups having at least one carbon-carbon triple bond, and having in the range of 2 up to about 100 carbon atoms, and "substituted alkynyl" refers to alkynyl groups further bearing one or more substituents as set forth below.

As used herein, "oxiranylene" refers to divalent moieties having the structure:

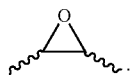

As used herein, "arylene" refers to a divalent aryl moiety. "Substituted arylene" refers to arylene moieties bearing one or more substituents as set forth above.

As used herein, "acyl" refers to alkyl-carbonyl species.

"Allyl" as used herein, refers to refers to a compound bearing at least one moiety having the structure:

"Imide" as used herein, refers to a functional group having two carbonyl groups bound to a primary amine or ammonia. The general formula of an imide of the invention is:

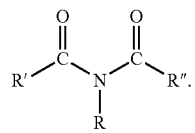

"Polyimides" are polymers of imide-containing monomers. Polyimides are typically linear or cyclic. Non-limiting examples of linear and cyclic (e.g. an aromatic heterocyclic polyimide) polyimides are shown below for illustrative purposes.

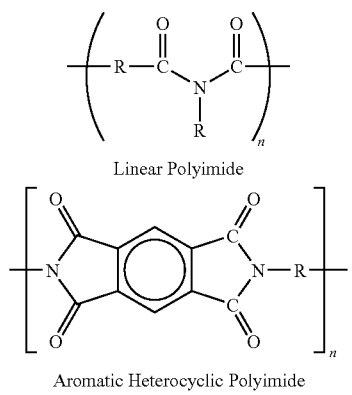

Linear Polyimide

Aromatic Heterocyclic Polyimide

"Maleimide," as used herein, refers to an N-substituted maleimide having the formula as shown below:

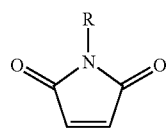

where R is an aromatic, heteroaromatic, aliphatic, or polymeric moiety.

"Bismaleimide" or "BMI", as used herein, refers to a polyimide having the general structure shown below:

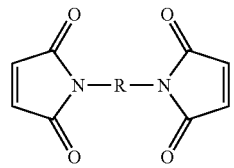

where R is an aromatic, heteroaromatic, aliphatic, or polymeric moiety.

BMIs can cure through an addition rather than a condensation reaction, thus avoiding problems resulting from the formation of volatiles. BMIs can be produced by a vinyl-type polymerization of a pre-polymer terminated with two maleimide groups.

As used herein, the term "acrylate" refers to a compound bearing at least one moiety having the structure:

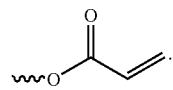

As used herein, the term "acrylamide" refers to a compound bearing at least one moiety having the structure:

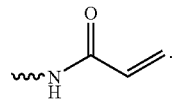

As used herein, the term "methacrylate" refers to a compound bearing at least one moiety having the structure:

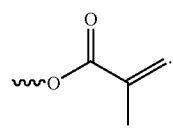

As used herein, the term "methacrylamide" refers to a compound bearing at least one moiety having the structure:

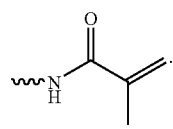

"Maleate" as used herein, refers to a compound bearing at least one moiety having the structure:

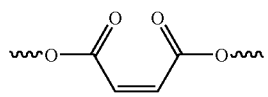

"Fumarate" as used herein, refers to a compound bearing at least one moiety having the structure:

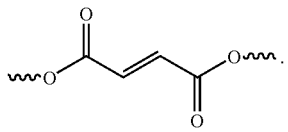

As used herein, the term "citraconimide" refers to a compound bearing at least one moiety having the structure:

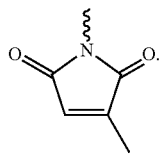

"Itaconate", as used herein refers to a compound bearing at least one moiety having the structure:

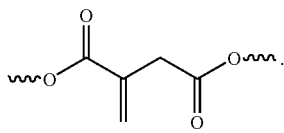

As used herein, the terms "halogen," "halide," or "halo" include fluorine, chlorine, bromine, and iodine.

As used herein, "siloxane" refers to any compound containing a Si—O moiety. In certain embodiments, siloxanes of the invention include 2 or more repeating units of Si—O. Exemplary cyclic siloxanes include hexamethylcyclotrisiloxane, octamethylcyclotetrasiloxane, decamethylcyclopentasiloxane, dodecamethylcyclohexasiloxane and the like.

As used herein "epoxy" refers to a thermosetting epoxide polymer that cures by polymerization and crosslinking when mixed with a catalyzing agent or "hardener," also referred to as a "curing agent" or "curative." Epoxies of the present invention include, but are not limited to aliphatic, cycloaliphatic, glycidyl ether, glycidyl ester, glycidyl amine epoxies, and the like, and combinations thereof. Epoxies of the invention include compounds bearing at least one moiety having the structure:

As used herein, the term "oxetane" refers to a compound bearing at least one moiety having the structure:

As used herein, the term "vinyl ether" refers to a compound bearing at least one moiety having the structure:

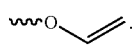

As used herein, the term "vinyl ester" refers to a compound bearing at least one moiety having the structure:

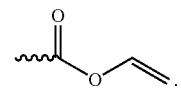

As used herein, "styrenic" refers to a compound bearing at least one moiety having the structure:

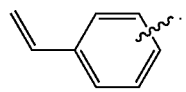

"Oxazoline" as used herein, refers to a compound bearing at least one moiety having the structure:

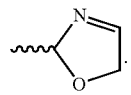

"Benzoxazine" as used herein, refers to a compound bearing at least one moiety having the structure:

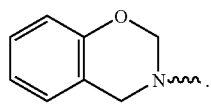

"Propargyl" as used herein, refers to a compound bearing at least one moiety having the structure:

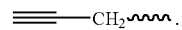

"Cyanate" as used herein, refers to a compound bearing at least one moiety having the structure:

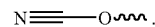

As used herein, "norbornyl" refers to a compound bearing at least one moiety having the structure:

As used herein, the term "free radical initiator" refers to any chemical species which, upon exposure to sufficient energy (e.g., light, heat, or the like), decomposes into parts which are uncharged, but every one of such part possesses at least one unpaired electron.

As used herein, the term "coupling agent" refers to chemical species that are capable of bonding to a mineral surface and which also contain polymerizably reactive functional group(s) so as to enable interaction with the adhesive composition. Coupling agents thus facilitate linkage of the die-attach paste to the substrate to which it is applied.

"Diamine," as used herein, refers generally to a compound or mixture of compounds, where each species has 2 amine groups.

A "diol" according to the present invention, is a compound containing two hydroxyl groups (—OH groups); while "polyol" refers to alcohols containing multiple hydroxyl groups.

The term "solvent," as used herein, refers to a liquid that dissolves a solid, liquid, or gaseous solute, resulting in a solution. "Co-solvent" refers to a second, third, etc. solvent used with a primary solvent.

As used herein, "acid catalyst" refers to any acidic substance or compound that, when added to a chemical reaction, has the effect of accelerating, increasing the rate or yield of the reaction without being consumed by the overall reaction. Typically, an acid catalyst will contain a single acid, but mixtures comprising two or more acids are contemplated for use in the present invention. Acid catalysts of the invention can be soluble or insoluble. For example, polymer-bound acid catalysts may conveniently be used in the methods of the invention and then easily removed e.g. by gravity filtration.

"Glass transition temperature" or "$T_g$": is used herein to refer to the temperature at which an amorphous solid, such as a polymer, becomes brittle on cooling, or soft on heating. More specifically, it defines a pseudo second order phase transition in which a supercooled melt yields, on cooling, a glassy structure and properties similar to those of crystalline materials e.g. of an isotropic solid material.

"Modulus" or "Young's modulus" as used herein, is a measure of the stiffness of a material. Within the limits of elasticity, modulus is the ratio of the linear stress to the linear strain which can be determined from the slope of a stress-strain curve created during tensile testing.

The "Coefficient of Thermal Expansion" or "CTE" is a term of art describing a thermodynamic property of a substance. The CTE relates a change in temperature to the change in a material's linear dimensions. As used herein "$\alpha_1$ CTE" or "$\alpha_1$" refers to the CTE before the $T_g$, while "$\alpha_2$ CTE" refers to the CTE after the $T_g$.

"Thixotropy" as used herein, refers to the property of a material which enables it to stiffen or thicken in a relatively short time upon standing, but upon agitation or manipulation to change to low-viscosity fluid; the longer the fluid undergoes shear stress, the lower its viscosity. Thixotropic materials are therefore gel-like at rest but fluid when agitated and have high static shear strength and low dynamic shear strength, at the same time.

"Thermogravimetric analysis" or "TGA" refers to a method of testing and analyzing a material to determine changes in weight of a sample that is being heated in relation to change in temperature. "Decomposition onset" refers to a temperature when the loss of weight in response to the increase of the temperature indicates that the sample is beginning to degrade.

The invention is based on the discovery that the compounds and compositions described herein are useful as high performance monomers in thermoset adhesives and resins useful for the electronic packaging industry.

The invention provides hetero-functional monomers containing at least one electron rich olefinic bond and at least one electron poor olefinic bond. As used herein, "olefinic bond" refers to a carbon-carbon double bond. The characterization of an olefinic bond as "electron rich" or "electron poor" is meant to specify that the olefinic bond has a nature of an electron donor or an electron acceptor, respectively.

In certain embodiments, this type of monomer can be used as a co-monomer in a free-radical cure mechanisms via reaction of both the electron rich and electron poor double bonds. In other embodiments the monomers described herein are selectively polymerized only through their electron rich olefinic moieties via a cationic cure mechanism. The resulting oligomers and polymers thereby retain pendant, polymerizable, electron poor olefinic moieties. These functional oligomers and polymers are useful additives or base components in thermoset adhesives and resins. In certain embodiments, the hetero-functional monomers containing one or more electron rich carbon-carbon double bond and one or more electron poor double bond can act as a co-monomer in a thermoset composition with a maleimide monomer. In some embodiments, the thermoset composition contains bismaleimide resins.

According to embodiments of the present invention, compounds are provided in which at least one olefinic moiety having an electron rich double bond is connected to at least one olefinic moiety having an electron poor double bond, via a linking moiety. The olefinic moiety that includes an electron rich double bond may be an unsubstituted or a substituted group and, if substituted, a substituent is an acyclic group. Non-limiting examples of an olefinic moiety that includes an electron rich double bond include vinyl ether or allyl ether.

The olefinic moiety that includes an electron poor double bond may be derived from an unsaturated compound having a carbonyl group or another electrophilic entity. Non-limiting examples of an olefinic moiety that includes an electron poor double bond include maleate, fumarate, maleimide, acrylate, or methacrylate.

The linking moiety (also occasionally referred to as "a spacer group") mentioned above comprises a $C_3$ to about $C_{500}$ aliphatic, cycloaliphatic, or aromatic group, such as, a $C_4$ to about $C_{500}$ aliphatic, cycloaliphatic, and aromatic group, for instance, a $C_6$ to about $C_{500}$ aliphatic, cycloaliphatic, and aromatic group, e.g., a $C_8$ to about $C_{500}$ aliphatic, cycloaliphatic, and aromatic group, or a $C_{12}$ to about $C_{500}$ aliphatic, cycloaliphatic, and aromatic group.

In compounds according to some embodiments of the invention, when the olefinic moiety that includes an electron poor double bond is an unsubstituted or a substituted maleimide group, the linking moiety does not include any carbonyl groups. In compounds according to other embodiments of the invention, the compounds may both contain an unsubstituted or a substituted maleimide group (as the olefinic moiety that includes an electron poor double bond) and have a linking moiety including a carbonyl group(s), as demonstrated by formula I below:

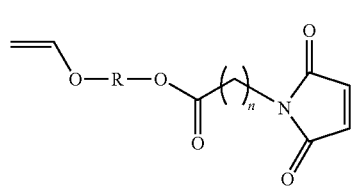

I where R is an alkylene moiety; and n is the integer having the value between 1 and 11.

In certain embodiments of the invention, n is 2-10. In other embodiments, n is 4-8. In yet further embodiments, n is 6-11.

Non-limiting examples of specific compounds according to the invention include compounds that are set forth below:

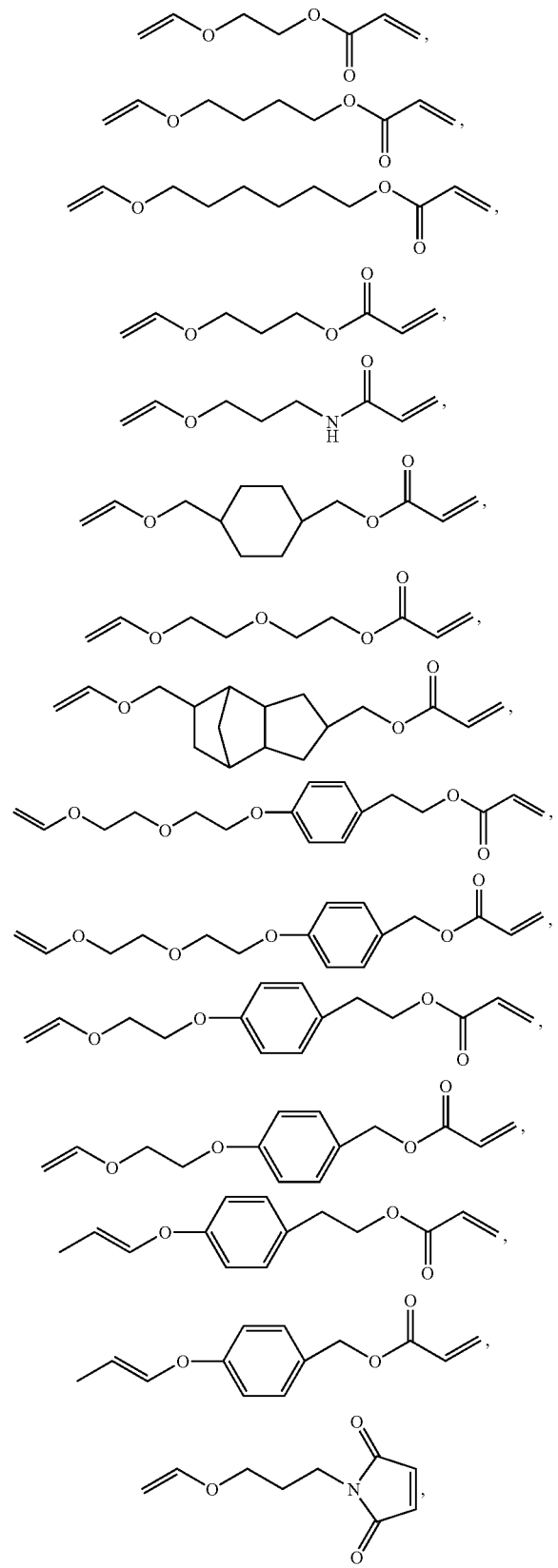

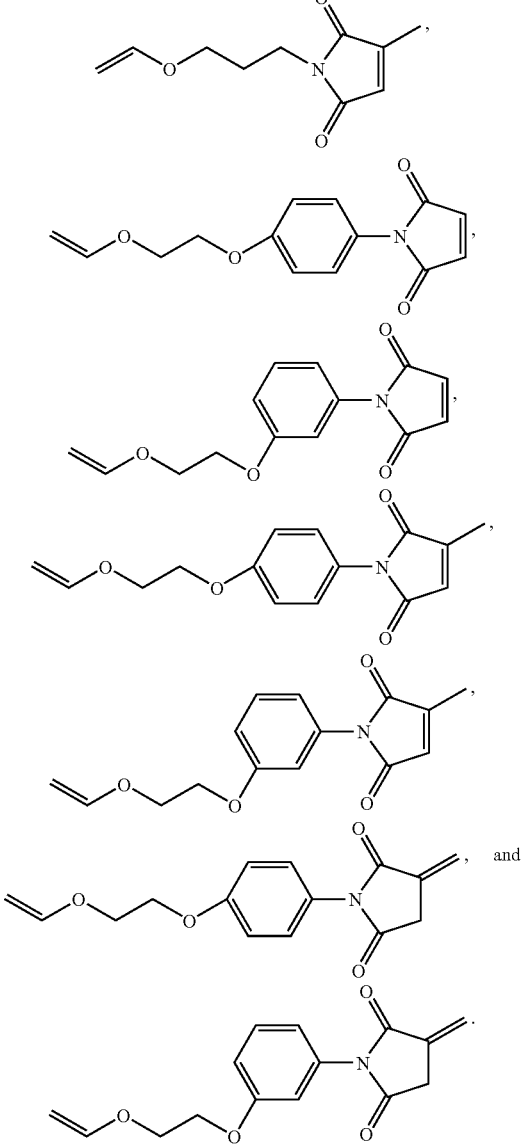

In another embodiment of the invention, adhesive compositions including invention compounds containing at least one electron rich carbon-carbon double bond and at least one electron poor double bond, and optionally at least one curing initiator are provided. These materials are useful as thermosetting monomers that can be incorporated into adhesive compositions. In some embodiments, the adhesive compositions are useful in the microelectronic packaging industry.

In some embodiments the monomers of the invention can be used in two stage cures. For example, a cationic first stage cure can be followed by a second stage free-radical cure. The cationic cure will occur only through the pendant, electron rich, vinyl or propenyl ether functional groups and the resulting oligomer or polymer will have pendant, electron poor, ethylenically unsaturated moieties that can then be cured in a second stage free-radical cure. The cationic polymerization step may be photo or thermally initiated. This two-stage cure would be very useful for a "B-stageable" adhesive wherein the liquid monomers of this invention are applied to a substrate and then subjected to a cationic UV cure step to provide a non-tacky, thermoplastic coating on the substrate. This functional thermoplastic film is then re-liquified on a heated stage and a second component (e.g. a silicon device) can then be brought into intimate contact with the B-staged adhesive. A final thermal (free-radical) cure step is used to permanently bond the second component or device to the substrate.

It should be understood that other cationic monomers may be used to modify the properties of the initial B-stage film. Other mono-functional vinyl ethers, propenyl ethers, aliphatic epoxies, cycloaliphatic epoxies, and glycidyl ether epoxies may, for example, be formulated together with the monomers of this invention. Bi-functional and polyfunctional versions of these co-monomers may also be included at low levels to further modify the properties of these films.

In certain embodiments of the invention, it may also be desirable to include in the formulation co-monomers that contain only free-radically polymerizable moieties. A wide variety of such compounds are known in the art. Mono-, bi-, and poly-functional monomers and oligomers can be formulated into the adhesive composition. These could include, for example, mono-functional compounds, such as, mono-maleimides, or bismaleimides that can be included to increase the glass transition temperature of the final thermoset. Alternatively, the co-monomers can include end-functionalized rubber compounds that can be co-cured in the final step and thereby provide a tougher adhesive bond.

The present invention also provides methods for preparing functional, preformed oligomers and polymers. According to such methods, monomers of the invention alone, or in combination with other vinyl or propenyl ether monomer, are cationically polymerized exclusively through the vinyl or propenyl ether moieties. These functional polymers are then be isolated by standard precipitation techniques. Such polymers can be then formulated with a variety of free-radically polymerizable monomers for a variety of adhesive and/or matrix resin applications.

The monomers described herein can be used co-monomers in free-radical cures. While the electron poor moieties of these monomers will not undergo cationic cure, the electron rich vinyl or propenyl ether moieties can readily undergo co-cure under free-radical cure conditions. Thus, these monomers can be used alone, or in combination with other (meth) acrylate, maleimide, itaconimide, itaconate, citraconimide, fumarate, maleate, vinyl ester, styrenic, epoxy, oxetane, benzoxazine, or oxazoline monomers.

Cationic thermal and/or photoinitiators contemplated for use in this invention include bis(4-(diphenylsulphonio)-phenyl)sulfide bis-hexafluorophosphate; bis(4-(diphenylsulfono)-phenyl)sulfide bis-hexafluorophosphate; bis(4-(di(4-(2-hydroxyethyl)phenyl)sulfino-phenyl)sulfide bis-hexafluorophosphate; bis(4-(di(4-(2-hydroxyethyl)phenyl) sulfino)-phenyl)sulfide bis-hexafluoroantinomate; ($\eta^5$-2,4-(cyclopentadienyl){1,2,3,4,5,6-$\eta$)-methylethyl)-benzene}-iron(II) hexafluorophosphate; triarylsulfonium hexaflurophosphate; (tolcumyl)iodonium tetrakis(pentafluorophenyl)borate; and diaryl iodonium hexafluoroantimonate.

The present invention provides compounds bearing at least one acyclic electron rich olefinic bond and at least one electron poor olefinic bond, wherein the two olefinic bonds are separated by a $C_3$ to about $C_{500}$ aliphatic, cycloaliphatic, or aromatic spacer. The compounds of the invention possess vinyl ether or propenyl ether functional groups as the electron rich double bond.

Vinyl propenyl ethers and ethers are known for their ability to undergo facile polymerization in the presence of cationic initiators. The electron poor olefinic bonds of this invention do not participate in cationic polymerizations. All of the electron poor olefinic functional groups of this invention, can however, be readily polymerized in the presence of free radical initiation. Thus, in one embodiment of this invention, the cure of the inventive compounds can be accomplished in two stages to give a first stage (cationically initiated) conversion of these bifunctional monomers from a low molecular weight liquid state to a B-staged thermoplastic, followed by a second stage (free radically initiated) conversion of the B-staged thermoplastic to a cross-linked thermoset resin. In one preferred embodiment, the first (i.e. cationic) polymerization step is accomplished using a cationic photoinitiator, and the second (free-radical) polymerization step is achieved using a thermal (e.g. peroxide) free radical catalyst.

The ability of the invention compounds to be polymerized in this controlled, discrete, two-stage fashion provides some significant benefits in real world applications. One exemplary application where the independent dual cure feature of the inventive compounds can be used with great benefit is in the area of B-staged adhesives. The dual functional compounds of this invention, for example, can be formulated into low viscosity compositions that can be "spun onto" the back of a silicon wafer (one with active microelectronic devices on the opposite side). The resulting thin, uniform liquid adhesive composition comprising the invention compounds, a cationic photoinitiator, and a free radical thermal initiator can then be B-staged by exposure to ultra violet (UV) light of an appropriate wavelength to give a thermoplastic, non-tacky coating on the backside of the silicon wafer. The silicon wafer can then be diced to yield discrete microelectronic devices that possess a pre-applied adhesive on the backside. These devices can then be individually placed onto leadframes (or other suitable electronic packaging substrate) with the pre-applied adhesive layer placed in intimate contact with the leadframe surface and then thermally cured in place. The pre-applied thermoplastic adhesive layer at first becomes fluid—wetting the substrate and then cures, via free radical polymerization, to provide a permanent thermoset adhesive bond to the substrate.

Although the previous description specifically addresses the use of the invention compounds in an electronic materials application, it should be understood that a wide variety of potential applications exist for the pre-applied adhesives that can be derived from their use. The two-stage cure of the invention compounds could be used in a variety of automotive, marine, aerospace, and industrial adhesive applications. An important industrial application for dual stage cure of the invention compounds, for example, is in the area of threadlock adhesives. Compositions comprising invention compounds, a cationic photoinitiator, and a hydroperoxide initiator can be pre-applied as a thin film to bolt or pipe threads and fixed in place with UV irradiation using a similar method as described above. A combination of cationically polymerizable monomers (i.e. invention compounds as well as commercially available monomers) can then be formulated to render the final glass transition temperature of the thermoplastic, B-staged coating to around room temperature. The pre-coated thread can then be permanently secured in place by simply screwing it into any metal nut or equivalent appropriately threaded surface. The second stage thermoset reaction occurs via the decomposition (catalyzed by trace levels of transition metal ions present on the nut thread surface) of the hydroperoxide catalyst under the anerobic conditions produced when the bolt or pipe is screwed in place.

Compositions Containing Hetero-Functional Compounds

The present invention provides compositions containing at least one hetero-functional compound. In certain embodiments, the hetero-functional compound is a compound according to formula I, above. For example, the invention compound may be used independently as an adhesives or may be combined with other materials and reagents to prepare adhesive compositions. In certain embodiments, the invention compounds may be combined with other adhesives and/or resins to prepare adhesive compositions. A hetero-functional compound of the invention may be used as the sole thermoset/monomer of an adhesive composition of the invention. In other embodiments, a hetero-functional compound of the invention may be combined with other monomers, such as thermoset monomers, to make a fully formulated adhesive composition.

The hetero-functional monomers provided by the invention are useful in a variety of compositions and applications other than adhesives in the electronics field, including marine coatings, sports equipment manufacture, dental resins and adhesives, composite resins for aerospace, automotive, thread-lock adhesives, and marine applications, and the like. Furthermore, the hetero-functional monomers of this invention can be used to make oligomers and polymers bearing polymerizable functional groups, which would have utility in a variety of applications.

In certain embodiments of the invention, a heterofuntional compound of the invention, such as a compound according to formula I, is present in a composition, such as an adhesive composition, in an amount from 0.5 weight percent (wt %) to about 98 wt %, based on the total weight of the composition. Typically, the composition will contain an amount of the hetero-functional compound equal to at least about 5 wt %, often at least about 10 wt %, frequently at least about 20 wt %, and in some embodiments at least about 40 wt % based on the total weight of the composition.

In another embodiment of the invention, the composition containing the heterofuntional compound of the invention includes at least one co-monomer, which is typically present in an amount from 10 wt % to about 90 wt %, based on the total weight of the composition. In some aspects of the invention, the composition will contain an amount of the co-monomer equal to at least about 15 wt %, often at least about 20 wt %, frequently at least about 25 wt %, and in some embodiments at least about 30 wt % based on the total weight of the composition. Co-monomers suitable for use in the compositions according to the invention include, but are not limited to, acrylates, acrylamides, methacrylates, methacrylamides, cyanate esters, maleimides, vinyl ethers, vinyl esters, styrenic compounds, allyl functional compounds, and olefins.

Curing and Curing Initiators. The invention compositions described herein can be cured in a variety of ways with or without a catalyst. The invention compounds can also serve as a useful class of monomers for free radical cure. Vinyl and propenyl ether functional groups are not, by themselves, generally capable of being polymerized by free radical initiation. A synergist, alternating co-cure between electron rich and electron poor olefinic monomers, however, is known to occur. The invention compounds contain both electron rich and electron poor olefinic substituents in the same molecule. This makes them ideal candidates for alternating co-cures because the two different types of polymerizable carbon-carbon double bonds are always present in a one to one equivalent ratio.

Combinations of vinyl and propenyl ethers with aliphatic maleimide monomers can be polymerized simply via exposure to certain wavelengths of UV radiation (specifically, the "UVB" portion of the spectrum centered around 310 nanometers). This light-induced polymerization reaction does not require the addition of any photoinitiator. Another advantageous feature that has been noted for this type of cure is its inherent resistance to oxygen poisoning. Therefore, the compounds of this invention that contain both maleimide vinyl ether and/or propenyl ether functionality can be used in photocure applications without a requirement for added photoinitiator to give tack-free cross-linked films and coatings. The invention compounds have a further advantage over simple physical mixtures of aliphatic maleimides and vinyl or propenyl ethers in that both the donor and acceptor carbon-carbon double bonds are present in each molecule and thus would not be subject to the performance drift that can arise from any mix ratio variation.

It should also be noted that the cure of invention compounds that contain both maleimide and vinyl ether or propenyl ether functional groups in the same molecule under UV exposure, without any requirement for a photoinitiator, would seem to preclude their use in the two stage cures described previously (where a cationic first stage cure is followed by a subsequent, free radical, second stage cure). The invention compounds can still be used, however, if a filter is used to screen out any UVB radiation during the first stage cure. Virtually every commercial cationic photocure initiator responds to UVA light wavelengths, so the use of filters to exclude the UVB portion of the spectrum would not necessarily have any negative impact the performance of these invention compounds in the two-stage cure application.

Thus, in certain embodiments, the present invention provides compositions, such as adhesive compositions, including at least one hetero-functional compound of the invention and at least one curing initiator. The curing initiator is typically present in adhesive compositions of the invention at an amount from 0.1 wt % to about 5 wt %, based on total weight of the composition, and is typically a free-radical initiator. In some embodiments, the curing initiator is present at least about 0.5 wt %, often at least about 1 wt %, frequently at least about 2 wt %, at in some embodiments at least about 3 wt %, based on total weight of the composition.

Free-radical initiators contemplated for use in the practice of the present invention typically decompose (i.e., have a half life in the range of about 10 hours) at temperatures in the range of about 70° C. up to 180° C. Exemplary free radical initiators contemplated for use in the practice of the present invention include peroxides (e.g. dicumyl peroxide, dibenzoyl peroxide, 2-butanone peroxide, tert-butyl perbenzoate, di-tert-butyl peroxide, 2,5-bis(tert-butylperoxy)-2,5-dimethylhexane, bis(tert-butyl peroxyisopropyl)benzene, and tert-butyl hydroperoxide), azo compounds (e.g., 2,2'-azobis(2-methyl-propanenitrile), 2,2'-azobis(2-methylbutanenitrile), and 1,1'-azobis(cyclohexanecarbonitrile)). Other free-radical initiators that will be well-known in the art may also be suitable for use in the compositions of the present invention.

Photoinitiators. Free radical initiators also include photoinitiators. For invention compositions that contain a photoinitiator, the curing process can be initiated, for example, by UV radiation. In one embodiment, the photoinitiator is present at a concentration of 0.1 wt % to 5 wt %, based on the total weight of the organic compounds in the composition (excluding any filler). In one embodiment, the photoinitiator comprises 0.5 wt % to 3.0 wt %, based on the total weight of the organic compounds in the composition. In other embodiments, the photoinitiator is present at least about 0.5 wt %, often at least about 1 wt %, frequently at least about 2 wt %, and in some embodiments at least about 3 wt %, based on the total weight of the organic compounds in the composition. Photoinitiators include benzoin derivatives, benzilketals, α,α-dialkoxyacetophenones, α-hydroxyalkylphenones, α-aminoalkylphenones, acylphosphine oxides, titanocene compounds, combinations of benzophenones and amines or Michler's ketone, and the like.

In some embodiments, both photoinitiation and thermal initiation may be desirable. For example, curing of a photoinitiator-containing adhesive can be started by UV irradiation, and in a later processing step, curing can be completed by the application of heat to accomplish a free-radical cure. Both UV and thermal initiators may therefore be added to the adhesive compositions of the invention.

In other embodiments the initiator is an anionic catalyst. Examples of anionic initiators include Lewis bases such as tertiary amines and imidazoles. Specific examples include benzyldimethlamine, triethylamine, tripropylamine, pyridine, dimethylaminopyridine, dimethylethanolamine, diethylethanolamine, tributylamine, 2-methylimidazole, 2-undecylimidazole, 1-benzyl-2-methylimidazole, 1-cyanoethyl-2-methylimidazole, 1-cyanoethyl-2-phenylimidazole, 1-cyanoethyl-2-undecylimidazole, 1-cyanoethyl-2-ethyl-4-methylimidazole, 1-cyanoethyl-2-isopropylimidazole, 1-cyanoethyl-2-methylimidazole-trimellitate, 1-cyanoethyl-2-phenylimidazole-trimellitate, 1-cyanoethyl-2-ethyl-4-methylimidazole-trimellitate, 1-cyanoethyl-2-undecylimidazole-trimellitate, 2,4-diamino-6-(2'methylimidazolyl-(1')) ethyl-s-triazine, 2,4-diamino-6-(2'-ethyl-4'-methylimidazolyl-(1'))ethyl-s-triazine, 2,4-diamino-6-(2'-undecylimidazolyl-(1'))ethyl-s-triazine, 2-phenyl-4-methyl-5-hydroxymethylimidazole, 2-phenyl-4,5-dihydroxymethylimidazole, 1-cyanoethyl-2-phenyl-4,5-di(cyanoethoxymethyl)imidazole, 2-methylimidazole—isocyanuric acid addition compound, 2-phenylimidazole—isocyanuric acid addition compound, 2,4-diamino-6[2'-methylimidazolyl-(1)']ethyl-s-triazine isocyanurate adduct, 4,4'-methylene-bis-(2-ethyl-5-methylimidazole), and the like.

In other embodiments the initiator is a cationic catalyst. Specific examples include onium compounds. Specific examples include bis[4-(diphenylsulphonio)-phenyl]sulphide bis-hexafluorophosphate, bis[4-(di(2-hydroxyethyl)phenyl)sulphonio-phenyl]sulphide bis-hexafluorophosphate, bis[4-(di(4-(2-hydroxyethyl)phenyl)sulphonio)phenyl]sulphide bis-hexafluoroantimonate, ($\eta^5$-2,4-(cyclopentadienyl)[(1,2,3,4,5,6-$\eta$)-(methylethyl)-benzene]-iron(II) hexafluorophosphate, triarylsulphonium hexafluorophosphate, (tolylcumyl)iodonium tetrakis(pentafluorophenyl)borate, diaryl iodonium hexafluoroantimonate, and the like. In certain embodiments, the invention provides adhesive compositions including 0.5 wt % to about 98 wt % of at least one compound described herein, based on total weight of the composition; optionally, 10 wt % o about 90 wt % of at least one co-monomer selected from acrylates, methacrylates, maleimides, vinyl ethers, vinyl esters, styrenic compounds, allyl functional compounds, and olefins, based on total weight of the composition; 0 to about 90 wt % of a conductive filler; 0.1 wt % to about 5 wt % of at least one curing initiator, based on total weight of the composition; and 0.1 wt % to about 4 wt %, of at least one coupling agent, based on total weight of the composition.

Additional Co-Curing Compounds. In certain aspects, the adhesive compositions of the invention include at least one additional compound that can co-cure with the hetero-functional compound. The additional compound is typically present in the adhesive compositions from about 10 wt % to about 90 wt % based on total weight of the composition. In such aspects, the composition will typically contain an amount of the co-curing compound equal to at least about 20 wt %, often at least about 30 wt %, frequently at least about 40 wt %, and in some embodiments at least about 50 wt % based on the total weight of the composition. Such compounds include, for example, epoxies (e.g. epoxies based on glydicyl ethers of alcohols, phenols, bisphenols, oligomeric phenolics, phenolic novolacs, cresolic novolacs, acrylates, methacrylates, maleimides, poly-phenol compounds (e.g. poly(4-hydroxystyrene)), anhydrides, dianhydrides, polyanhydrides such as styrene-maleic anhydride co-polymers, imides, carboxylic acids, dithiols, polythiols, phenol functional monomaleimides, bismaleimides, polymaleimides, mono-itaconates, mono-maleates, mono-fumarates, acrylic acid, methacrylic acid, cyanate esters, vinyl ethers, vinyl esters, or phenol functional esters, ureas, amides, polyolefins (e.g. amine, carboxylic acid, hydroxy, and epoxy functional) siloxanes (e.g. epoxy, phenolic, carboxylic acid, or thiol functional), cyanoacrylates, allyl functional compounds and styrenic, as well as combinations thereof.

Coupling Agents. In certain aspects, the adhesive compositions of the invention include at least one additional coupling agent. Exemplary coupling agents contemplated for use in the practice of the present invention include silicate esters, metal acrylate salts (e.g., aluminum methacrylate), titanates (e.g., titanium methacryloxyethylacetoacetate triisopropoxide), zirconates, or compounds that contain a copolymerizable group and a chelating ligand (e.g., phosphine, mercaptan, acetoacetate, and the like). In some embodiments, the coupling agent contains both a co-polymerizable function (e.g., vinyl, acrylate, methacrylate, epoxy, thiol, anhydride, isocyanate, and phenol moieties) and a silicate ester function. The silicate ester portion of the coupling agent is capable of condensing with metal hydroxides present on the mineral surface of substrate, while the co-polymerizable function is capable of co-polymerizing with the other reactive components of invention adhesive compositions, such as die-attach pastes. In certain embodiments coupling agents contemplated for use in the practice of the invention are oligomeric silicate coupling agents such as poly(methoxyvinylsiloxane).

Adhesive Paste Compositions Containing the Hetero-Functional Compound

In certain embodiments, the present invention provides adhesive compositions that are of various consistencies including, liquids, gels, pastes and solids. In one embodiment, the adhesive composition is a paste suitable for attaching an electronics die to a substrate (i.e., die-attach pastes). Die attach pastes of the invention are optimized for long-term reliability, rapid inline curing, long pot-life, viscosity and thixotropic control for fast automated dispensing and manufacturing.

In one embodiment, the present invention provides an adhesive composition that include 0.5 wt % to about 98 wt % based on total weight of the composition, of a hetero-functional compound such as a compound represented by structural formula I; 0 to about 90 wt % of a filler, based on total weight of the composition; 0.1 wt % to about 5 wt % of at least one curing initiator, based on total weight of the composition; and 0.1 wt % to about 4 wt %, of at least one coupling agent, based on total weight of the composition.

B-Stageable Adhesives

In certain embodiments, the adhesive compositions and die attach pastes of the invention are B-stageable. As used herein, "B-stageable" refers to the properties of an adhesive having a first solid phase followed by a tacky rubbery stage at elevated temperature, followed by yet another solid phase at an even higher temperature. The transition from the rubbery stage to the second solid phase is thermosetting. However, prior to that, the thermosetting material behaves similarly to a thermoplastic material. Thus, such adhesives allow for low lamination temperatures while providing high thermal stability.

The B-stageable adhesive can be dispensed onto a die or a substrate by a variety of methods well known to those skilled in the art. In some embodiments, the adhesive is cast from solution using techniques such as spin coating, spray coating, stencil printing, screen printing, and the like. This dual stage cure is especially attractive for applications were it is desirable to apply an adhesive in liquid form, cure the material to a non-tacky thermoplastic state, and then cure this B-staged adhesive in a final heating step to bond two or more parts together. Thus, this dual stage cure method of the invention is particularly advantageous for silicon wafer back coatings. The original adhesive mixture can be spin coated onto the back of a silicon wafer. The coating can then be B-staged with heat or light. The coated wafers can then be diced to yield individual microelectronic components, which may be thermally attached directly to a substrate, and/or stacked together. The thermal "tacking step" re-liquifies the adhesive coating and provides a thermoplastic bond between the parts. The final bonding step involves a thermal (or in some cases light-based) cure to cross-link the B-staged adhesive composition. This method of assembly is highly desirable because it is easier to manufacture (especially for stacked die) than a traditional liquid adhesive assembly, and is much less expensive and wasteful compared to film-based adhesive technology.

In certain embodiments, a solvent may be employed in the practice of the invention. For example, when the B-stageable adhesive is spin-coated onto a circular wafer, it is desirable to have an even coating throughout the entire wafer, i.e., the solvent or solvent system should have the ability to deliver the same amount of adhesive to each point on the wafer. Thus, the adhesive will be evenly coated throughout, i.e., there will be the same amount of material at the center of the wafer as at the edges. Ideally, the adhesive is "Newtonian", with a thixotropic slope of 1.0. In certain embodiments, the solvent or solvent systems used to dispense the B-stageable adhesive have slopes ranging from 1.0 to about 1.2.

In some instances, the B-stageable adhesive is dispensed onto the backside of a die that has been coated with a polyimide. Thus, the solvent or solvent system used to dispense the B-stageable adhesive should not have any deleterious effects on the polyimide coating. To achieve this goal, in certain embodiments, the solvent system will include a polar solvent in combination with a nonpolar solvent. Typically, the polar solvent is suitable for use with the hetero-functional compound described herein in B-stageable adhesives, and the nonpolar solvent is a non-solvent for the hetero-functional compound. In addition, the polar solvent typically has a lower boiling point than the non-polar solvent. Without wishing to be to be limited to a particular theory, it is believed that when the adhesive is dispensed and then B-staged, the lower boiling polar solvent escapes first, leaving behind only the nonpolar non-solvent, essentially precipitating the oligomer uniformly and leaving the polyimide film undamaged.

In some embodiments, the solvent or solvent system has a boiling point ranging from about 150° C. up to about 300° C. In some embodiments, the solvent system is a combination of dimethyl phthalate (DMP), NOPAR 13, and terpineol. In other embodiments, the solvent system is a 1:1 (by volume) ratio of terpineol and NOPAR 13.

In general, adhesive compositions such as die-attach pastes and B-stageable adhesive compositions of the invention, will cure within a temperature range of 80-220° C., and curing will be effected within a length of time of less than 1 minute up to about 60 minutes. The B-stageable adhesive composition may be pre-applied onto either a semiconductor die or onto a substrate. As will be understood by those skilled in the art, the time and temperature curing profile for each adhesive composition will vary, and different compositions can be designed to provide the curing profile that will be suited to a particular industrial manufacturing process.

Additional Compounds. In certain embodiments, the compositions of the invention, such as adhesives (including die-attach paste adhesives), may contain modifiers that lend additional flexibility and toughness to the resultant cured adhesive. Such modifiers may be any thermoset or thermoplastic material having a $T_g$ of 50° C. or less, and typically will be a polymeric material characterized by free rotation about the chemical bonds, the presence of ether groups, and the absence of ring structures. Suitable such modifiers include polyacrylates, poly(butadiene), polyTHF (polymerized tetrahydrofuran, also known as poly(1,4-butanediol)), CTBN (carboxy-terminated butadiene-acrylonitrile) rubber, and polypropylene glycol. When present, toughening compounds may be present in an amount up to about 15 percent by weight of hetero-functional compound of the invention and any other monomer in the adhesive.

Inhibitors for free-radical cure may also be added to the adhesive compositions and die-attach pastes described herein to extend the useful shelf life. Examples of free-radical inhibitors include hindered phenols such as 2,6-di-tert-butyl-4-methylphenol; 2,6-di-tert-butyl-4-methoxyphenol; tert-butyl hydroquinone; tetrakis(methylene(3,5-di-tert-butyl-4-hydroxyhydrocinnamate))benzene; 2,2'-methylenebis(6-tert-butyl-p-cresol); and 1,3,5-trimethyl-2,4,6-tris(3',5'-di-tert-butyl-4-hydroxybenzyl)benzene. Other useful hydrogen-donating antioxidants such as derivatives of p-phenylenediamine and diphenylamine. It is also well know in the art that hydrogen-donating antioxidants may be synergistically combined with quinones and metal deactivators to make a very efficient inhibitor package. Examples of suitable quinones include benzoquinone, 2-tert butyl-1,4-benzoquinone; 2-phenyl-1,4-benzoquinone; naphthoquinone, and 2,5-dichloro-1,4-benzoquinone. Examples of metal deactivators include N,N'-bis(3,5-di-tert-butyl-4-hydroxyhydrocinnamoyl)hydrazine; oxalyl bis(benzylidenehydrazide); and N-phenyl-N'-(4-toluenesulfonyl)-p-phenylenediamine. Nitroxyl radical compounds such as TEMPO (2,2,6,6-tetramethyl-1-piperidnyloxy, free radical) are also effective as inhibitors at low concentrations. The total amount of antioxidant plus synergists typically falls in the range of 100 to 2000 ppm relative to the weight of total base resin. Other additives, such as adhesion promoters, in types and amounts known in the art, may also be added.

The adhesive compositions, such as die-attach paste adhesives, described herein will generally perform within the commercially acceptable ranges for die attach adhesives. Commercially acceptable values for die shear for the adhesives on a 80×80 mil² silicon die are in the range of greater than or equal to 1 kg at room temperature, and greater than or equal to 0.5 kg at 260° C. Acceptable values for warpage for a 500×500 mil² die are in the range of less than or equal to 70 Nm at room temperature.

Fillers. In some embodiments, fillers are contemplated for use in the practice of the present invention, which can be electrically conductive and/or thermally conductive, and/or fillers which act primarily to modify the rheology of the resulting composition. Examples of suitable electrically conductive fillers that can be employed in the practice of the present invention include silver, nickel, copper, aluminum, palladium, gold, graphite, metal-coated graphite (e.g., nickel-coated graphite, copper-coated graphite, and the like), and the like. Examples of suitable thermally conductive fillers that can be employed in the practice of the present invention include graphite, aluminum nitride, silicon carbide, boron nitride, diamond dust, zinc oxide, alumina, and the like. Compounds which act primarily to modify rheology include polysiloxanes (such as polydimethyl siloxanes), silica, fumed silica, fumed alumina, fumed titanium dioxide, calcium carbonate and the like.

Assemblies

The present invention also provides assemblies of components adhered together by the above-described adhesive compositions (e.g., B-stageable adhesives and die-attach pastes) of the invention. Thus, for example, assemblies comprising a first article adhered to a second article by a cured aliquot of an adhesive composition containing at least one hetero-functional compound are provided. Articles contemplated for assembly employing invention compositions include electronic components such as dies, memory devices (e.g. as flash memory devices), ASIC devices, microprocessors, and other microelectronic components. Assemblies also include microelectronic devices, such as copper lead frames, Alloy 42 lead frames, silicon dice, gallium arsenide dice, and germanium dice, that are adhered to a substrate by a cured aliquot of the above-described adhesive compositions Additional embodiments of the invention include adhesively bonded structures containing at least one hetero-functional compound described herein. Non-limiting examples of the adhesively bonded structures include electronic components bonded to a substrate, and circuit components bonded to printed wire boards. In other embodiments of the invention, articles of manufactures can be comprised substantially of a cured amount of the composition described herein, such as an industrial, marine, automotive, airline, aerospace, sporting goods, medical or dental article. Such articles of manufacture can also include fillers, extenders, pigments and/or reinforcing materials along with the compositions disclosed herein.

Conditions suitable to cure invention die attach paste adhesives include subjecting the above-described assembly to a temperature of less than about 200° C. for about 0.5 up to 2 minutes. This rapid, short duration heating can be accomplished in a variety of ways, e.g., with an in-line heated rail, a belt furnace, or the like. Optionally, the material can be oven cured at 150-220° C.

Methods of Using containing Hetero-Functional Compound and Adhesive Compositions According to the present invention, methods for adhesively attaching a first article to a second article are provided. Such methods can be performed, for example, by a) applying an adhesive composition of the invention to the first article, the second article or both the first and second articles; b) contacting the first article and the second article, where the first article and the second article are separated only by the adhesive composition applied in step a); and c) curing the adhesive composition applied in step a), thereby adhesively attaching the first article to the second article.

In one aspect of this method, the first and second articles are a semiconductor die and a substrate, respectively. Typically, according to this aspect the adhesive is a die attach paste. The method can include the steps of applying the adhesive composition (e.g. die attach paste) to the substrate, the semiconductor die, or both the substrate and the semiconductor die; b) melting the adhesive composition applied in step a); c) contacting the semiconductor device and the substrate, where the die and substrate are separated only by the adhesive composition applied in step a); and d) curing the adhesive composition applied in step a), thereby adhesively attaching the semiconductor device to the substrate. Applying the adhesive composition can include spin-coating, spray coating, stencil printing, screen printing and other methods well known in the art.

In still further embodiments, the invention provides B-stageable type methods for adhesively attaching a semiconductor die to a substrate. Such methods can be performed, for example, by applying an invention adhesive composition to the substrate, the semiconductor device or both the substrate and the semiconductor device; melting the applied adhesive composition applied; (c) contacting the semiconductor device and the substrate, such that the die and substrate are separated only by the applied adhesive composition; and curing the applied adhesive composition, thereby attaching the semiconductor device to the substrate.

The invention will now be further described with reference to the following non-limiting examples.

EXAMPLES

Example 1

Synthesis of 4-Acryloxybutylvinyl Ether

A 125 milliliter single-neck flask was charged with 11.6 grams (100 millimole) 4-hydroxybutylvinyl ether, 15.4 grams (150 millimoles) triethylamine, and twenty milliliters tetrahydrofuran. This solution was stirred magnetically and cooled in an ice bath. A solution of 9.05 grams (105 millimoles) acryloyl chloride dissolved in 20 milliliters THF was then dripped in over the course of forty-five minutes. The mix was stirred another hour while the temperature was allowed to rise to room temperature. The THF and excess triethylamine were removed on the rotary evaporator. The residue was extracted with three 20 ml portions of toluene and the toluene phase was rinsed with 20 ml deionized water. The toluene phase was dried with ten grams anhydrous magnesium sulfate and the toluene was removed to yield a mobile yellow liquid. The product weighed 12.3 grams (72% of theory). This liquid had major IR absorptions at 1723, 1635, 1616, 1408, 1188, 959, 809, and 731 wavenumbers.

Example 2

Synthesis of Cyclohexane Dimethanol Mono-Methacrylate Mono-Vinyl Ether

A 500-ml round-bottomed flask equipped with a Teflon-coated magnetic stir bar and reflux condenser was charged with 34.0 g (200 mmol) of cyclohexane dimethanol monovinyl ether, followed by the addition of 34.0 g (220 mmol) of methacrylic anhydride. To the flask was added 150 g of hexane, and 20.2 g (200 mmol) of triethylamine. The solution was refluxed for 3 hours to complete the reaction. After cooling the amine salt was vacuum filtered. The clear solution was washed in a separatory funnel with 2×50 ml of water, followed by 1×50 ml of saturated sodium chloride solution. The solution was then dried over anhydrous sodium sulfate, and gravity filtered. The solvent was removed using a rotary evaporator, and 43.0 g (90.3% yield) of a low viscosity yellow liquid was obtained. The FTIR spectrum of the sample showed major bands at 2924, 1719, 1637, 1612, 1321, 1166, and 811 wavenumbers.

Example 3

Ethylene Glycol Mono-Maleimidoundecanoate Mono-Vinyl Ether

A 500-ml round bottomed flask equipped with a Teflon-coated magnetic stir-bar and a reflux condenser was charged with 19.0 g of ethylene glycol mono-maleimidoundecanoate (54.1 mmol), followed by the addition of a large excess of butyl-vinyl ether 250.0 g (2.5 mol). To the flask was also added 0.1 g of palladium acetate phenanthroline complex, and the solution was stirred at 60° C. for 14 hours. The excess butyl vinyl ether was completely removed using a rotary evaporator, and 100 g of toluene was added to the flask. The solution was flash filtered through 10 g of silica gel to remove the catalyst and unreacted starting material. The toluene was then removed using a rotary evaporator. Approximately 15 g of a yellow liquid was obtained, which solidified upon standing overnight. The FTIR of the sample showed major bands at 2924, 1735, 1664, 1619, 1172, 827, and 695.

What is claimed is:

1. A compound selected from the group consisting of:

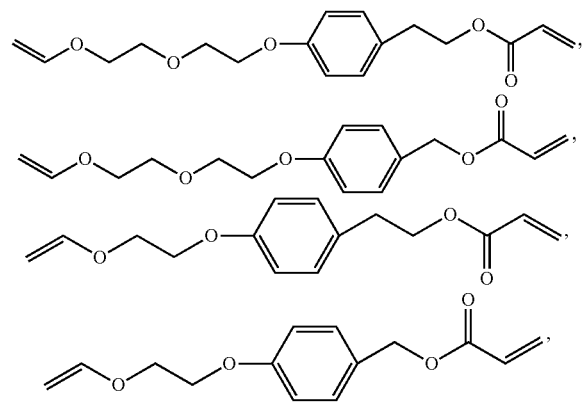

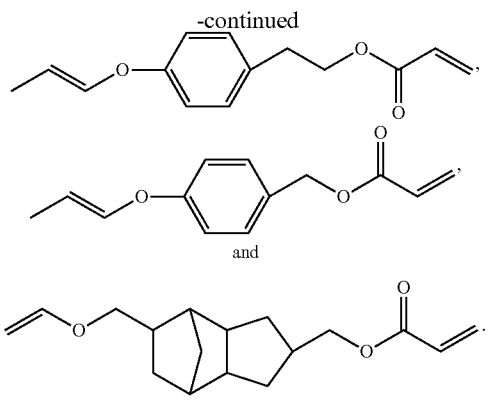

2. A composition comprising a compound of claim 1.

3. The composition of claim 2, further comprising at least one curing initiator, co-monomer, co-curing compound, coupling agent, or filler.

4. The composition of claim 3, wherein the co-monomer or co-curing compound is selected from the group consisting of epoxies, acrylates, methacrylates, maleimides, citraconimides, itaconimides, vinyl ethers, vinyl esters, styrenic compounds, itaconates, fumarates, allyl functional compounds, oxetanes, benzoxazines, and oxazolines.

5. The composition of claim 2, wherein the composition is an adhesive.

6. The composition of claim 2, wherein the composition is suitable for use in die-attach.

7. The composition of claim 2, wherein the composition is a coating.

* * * * *